(12) United States Patent
Bakács et al.

(10) Patent No.: US 8,398,969 B2
(45) Date of Patent: Mar. 19, 2013

(54) COMPOSITIONS AND METHODS FOR THE TREATMENT OF VIRAL HEPATITIS

(75) Inventors: Tibor Bakács, Budapest (HU); Imre Kövesdi, Rockville, MD (US); Vilmos Palya, Budapest (HU)

(73) Assignee: HepC Biotechnológiai Kutató és Fejlesztö Kft., Budapest (HU)

( * ) Notice: Subject to any disclaimer, the term of this patent is extended or adjusted under 35 U.S.C. 154(b) by 613 days.

(21) Appl. No.: 12/475,127

(22) Filed: May 29, 2009

(65) Prior Publication Data

US 2009/0291063 A1     Nov. 26, 2009

Related U.S. Application Data

(63) Continuation-in-part of application No. PCT/IB2007/054742, filed on Nov. 22, 2007.

(30) Foreign Application Priority Data

Dec. 1, 2006   (HU) .................................... 0600894

(51) Int. Cl.
   *C12N 7/04*      (2006.01)
   *A61K 48/00*    (2006.01)
   *A61K 39/12*    (2006.01)
(52) U.S. Cl. ................ 424/93.2; 424/204.1; 435/91.33; 435/236; 514/44 R
(58) Field of Classification Search .................. None
See application file for complete search history.

(56) References Cited

U.S. PATENT DOCUMENTS

| | | | |
|---|---|---|---|
| 5,124,148 A | 6/1992 | Csatary et al. | |
| 5,215,745 A | 6/1993 | Csatary et al. | |
| 5,602,023 A | 2/1997 | Csatary | |
| 5,871,744 A | 2/1999 | Vakharia et al. | |
| 6,225,289 B1 | 5/2001 | Kovesdi et al. | |
| 6,514,943 B2 | 2/2003 | Kovesdi et al. | |
| 6,596,280 B1 | 7/2003 | Vakharia et al. | |
| 7,022,327 B1 * | 4/2006 | Lutticken et al. | 424/204.1 |
| 7,195,896 B2 | 3/2007 | Kovesdi et al. | |
| 2007/0178563 A1 * | 8/2007 | Boot et al. | 435/91.1 |

FOREIGN PATENT DOCUMENTS

WO           8600529           1/1986

OTHER PUBLICATIONS

Ben Abdeljelil N. et al. (2008). Efficient rescue of infectious bursal disease virus using a simplified RNA polymerase II-based reverse genetics strategy. Arch Virol 153: 1131-1137.
Bayliss, C.D. et al. (1990). A comparison of the sequences of segment A of four infectious bursal disease virus strains and identification of a variable region in VP2. J Gen Virol, 71, 1303-1312.
Bakacs, T. et al. (2002). Intentional superinfection of decompensated chronic viral hepatitis by avian infectious bursal disease virus shows promise. Paper presented at: Cancer Detection and Prevention.
Bakacs, T. et al. (2004). Examination of the value of treatment of decompensated viral hepatitis patients by intentionally coinfecting them with an apathogenic IBDV and using the lessons learnt to seriously consider treating patients infected with HIV using the apathogenic hepatitis G virus. Vaccine 23, 3-13.
Boot, H. J. et al. (2001). Comparison of RNA and cDNA transfection methods for rescue of infectious bursal disease virus. J Virol Methods 97, 67-76.
Boot, H. J. et al. (2000). Rescue of very virulent and mosaic infectious bursal disease virus from cloned cDNA: VP2 is not the sole determinant of the very virulent phenotype. J Virol 74, 6701-6711.
Csatary, L. K. et al. (1984). Interference between human hepatitis A virus and an attenuated apathogenic avian virus. Acta Microbiol Hung 31, 153-158.
Csatary, L. K. et al. (1999). Successful treatment of decompensated chronic viral hepatitis by bursal disease virus vaccine. Anticancer Res 19, 629-633.
Csatary, L. K. et al. (1998). Preliminary report of a controlled trial of MTH-68/B virus vaccine treatment in acute B and C hepatitis: a phase II study. Anticancer Res 18, 1279-1282.
Galle, P. R. et al. (1988). Production of infectious duck hepatitis B virus in a human hepatoma cell line. J Virol 62, 1736-1740.
Jackwood, D. J. et al. (2002). Identification of infectious bursal disease virus quasispecies in commercial vaccines and field isolates of this double-stranded RNA virus. Virology 304, 105-113.
Kibenge, F. S. et al. (1988a). Biochemistry and immunology of infectious bursal disease virus. J Gen Virol 69 ( Pt 8), 1757-1775.
Kibenge F.S. et al. (1988b). Growth of serotypes I and II and variant strains of infectious bursal disease virus in Vero cells. Avian Dis 32: 298-303.
Kwon H.M. et al. (2004). Sequence analysis of the variable VP2 gene of infectious bursal disease viruses passaged in Vero cells. Virus Genes 28: 285-291.
Lim B.L. et al. (1999). Adaptation of very virulent infectious bursal disease virus to chicken embryonic fibroblasts by site-directed mutagenesis of residues 279 and 284 of viral coat protein VP2. J Virol 73: 2854-2862.
Mundt, E. et al. (1997). VP5 of infectious bursal disease virus is not essential for viral replication in cell culture. J Virol 71, 5647-5651.
Mundt, E. et al. (1996). Synthetic transcripts of double-stranded Birnavirus genome are infectious. Proc Natl Acad Sci U S A 93, 11131-11136.
Pedersden, K. A. et al. (1990). Detection of antibody to avian viruses in human populations. Epidemiol Infect 104, 519-525.

(Continued)

*Primary Examiner* — Maria Marvich
(74) *Attorney, Agent, or Firm* — Jason D. Voight

(57) ABSTRACT

The present invention discloses a novel apathogenic viral strain useful in the treatment of viral hepatitis infections. The preferred viral strain of Infectious Bursal Disease Virus (IBDV) is specifically characterized in terms of structure and biological activities. The invention also provides recombinant IBDV viral vectors for the inclusion of exogenous nucleic acid sequences enhancing the viral replication inhibitory effect of the virus of the invention. Preferably, the viral vector comprises a nucleic acid sequence encoding a cytokine. A method of treating viral hepatitis in a host comprising administering an anti-hepatitis effective amount of the IBDV strain of the present invention also provided.

7 Claims, 8 Drawing Sheets

OTHER PUBLICATIONS

Walters, K-A. et al. (2004). Superinfection Exclusion in Duck Hepatitis B Virus Infection Is Mediated by the Large Surface Antigen. J Virol 78, 7925-7937.

Wong, E-T. et al. (2002) Improved co-expression of multiple genes in vectors containing internal ribosome entry sites (IRESes) from human genes. Gene Therapy 9, 337-344.

Ye J, Chen Q, Zhou J. et al. (2007). Cloned Vero cell lines transfected with full-length A-segment or ORF1 cDNA sequence of IBDV. Cell Biol Int 31: 165-172.

Zierenberg, K. et al. (2004). Generation of serotype 1/serotype 2 reassortant viruses of the infectious bursal disease virus and their investigation in vitro and in vivo. Virus Res 105, 23-34.

* cited by examiner

```
1 GGATACGATCGGTCTGACCCCGGGGGAGTCACCCGGGGACAGGCCGTCAAGGCTTTGTTCCAGGATGGAA
CTCCTCCTTCTACAACGCTATCATTGATGGTCAGTAGAGATCAGACAAACGATCGCAGCGATGACAAACCTG
CAAGATCAAACCCAACAGATTGTTCCGTTCATACGGAGCCTTCTGATGCCAACAACCGGACCGGCGTCCATT
CCGGACGACACCCTGGAGAAGCACACTCTCAGGTCAGAGACCTCGACCTACAATTTGACTGTGGGGACACA
GGGTCAGGGCTAATTGTCTTTTTCCCTGGATTCCCTGGCTCAATTGTGGGTGCTCACTACACACTGCAGAGC
AATGGGAACTACAAGTTCGATCAGATGCTCCTGACTGCCCAGAACCTACCGGCCAGTTACAACTACTGCAGG
CTAGTGAGTCGGAGTCTCACAGTGAGGTCAAGCACACTTCCTGGTGGCGTTTATGCACTAAACGGCACCATA
AACGCCGTGACCTTCCAAGGAAGCCTGAGTGAACTGACAGATGTTAGCTACAATGGGTTGATGTCTGCAACA
GCCAACATCAACGACAAAATTGGGAACGTCCTAGTAGGGGAAGGGGTCACCGTCCTCAGCTTACCCACATCA
TATGATCTTGGGTATGTGAGGCTTGGTGACCCCATTCCCGCAATAGGGCTTGACCCAAAAATGGTAGCCACA
TGTGACAGCAGTGACAGGCCCAGAGTCTACACCATAACTGCAGCCGATGATTACCAATTCTCATCACAGTAC
CAACCAGGTGGGGTAACAATCACACTGTTCTCAGCCAACATTGATGCCATCACAAGCCTCAGCGTTGGGGGA
GAGCTCGTGTTTCAAACAAGCGTCCACGGCATTGTACTGGGCGCCACCATCTACCTCATAGGCTTTGATGGG
ACAGCGGTAATCACCAGGGCTGTGGCCGCAAACAATGGGCTGACGACCGGCACCGACAACCTTATGCCATTC
AATCTTGTGATTCCAACAAACGAGATAACCCAGCCAATCACATCCATCAAACTGGAGATAGTGACCTCCAAA
AGTGGTGGTCAGGCAGGGGATCAGATGTCATGGTCGGCAAGAGGGAGCCTAGCAGTGACGATCCATGGTGGC
AACTATCCAGGGGCCCTCCGTCCCGTCACGCTAGTGGCCTACGAAAGAGTGGCAACAGGATCCGTCGTTACG
GTCGCTGGGGTGAGCAACTTCGAGCTGATCCCAAATCCTGAACTAGCAAAGAACCTGGTTACAGAATACGGC
CGATTTGACCCAGGAGCCATGAACTACACAAAATTGATACTGAGTGAGAGGGACCGTCTTGGCATCAAGACC
GTCTGGCCAACAAGGGAGTACACTGACTTTCGTGAATACTTCATGGAGGTGGCCGACCTCAACTCTCCCCTG
AAGATTGCAGGAGCCTTCGGCTTCAAAGACATAATCCGGGCCATAAGGAGGATAGCTGTGCCGGTGGTCTCC
ACATTGTTCCCACCTGCCGCTCCCCTAGCCCATGCAATTGGGGAAGGTGTAGACTACCTGCTGGGCGATGAG
GCACAGGCTGCTTCAGGAACTGCTCGAGCCGCGTCAGGAAAAGCAAGAGCTGCCTCAGGCCGCATAAGGCAG
CTGACTCTCGCCGCCGACAAGGGGTACGAGGTAGTCGCGAATCTATTCCAGGTGCCCCAGAATCCCGTAGTC
GACGGGATTCTTGCTTCACCTGGGGTACTCCGCGGTGCACACAACCTCGACTGCGTGTTAAGAGAGGGTGCC
ACGCTATTCCCTGTGGTTATTACGACAGTGGAAGACGCCATGACACCCAAAGCATTGAACAGCAAAATGTTT
GCTGTCATTGAAGGCGTGCGAGAAGACCTCCAACCTCCATCTCAAAGAGGATCCTTCATACGAACTCTCTCT
GGACACAGAGTCTATGGATATGCTCCAGATGGGGTACTTCCACTGGAGACTGGGAGAGACTACACCGTTGTC
CCAATAGATGATGTCTGGGACGACAGCATTATGCTGTCCAAAGATCCCATACCTCCTATTGTGGGAAACAGT
GGAAATCTAGCCATAGCTTACATGGATGTGTTTCGACCCAAAGTCCCAATCCATGTGGCTATGACGGGAGCC
CTCAATGCTTGTGGCGAGATTGAGAAAGTAAGCTTTAGAAGCACCAAGCTCGCCACTGCACACCGACTTGGC
CTTAAGTTGGCTGGTCCCGGAGCATTCGATGTAAACACCGGGCCCAACTGGGCAACGTTCATCAAACGTTTC
CCTCACAATCCACGCGACTGGGACAGGCTCCCCTACCTCAACCTACCATACCTTCCACCCAATGCACGACGC
CAGTACCACCTTGCCATGGCTGCATCAGAGTTCAAAGAGACCCCCGAACTCGAGAGTGCCGTCAGAGCAATG
GAAGCAGCAGCCAACGTGGACCCACTATTCCAATCTGCACTCAGTGTGTTCATGTGGCTGGAAGAGAATGGG
ATTGTGACTGACATGGCCAACTTCGCACTCAGCGACCCGAACGCCCATCGGATGCGAAATTTTCTTCCAAAC
GCACCACAAGCAGGCAGCAAGTCGCAAAGGGCCAAGTACGGGACAGCAGGCTACGAGTGGAGGCTCGGGGC
CCCACACCAGAGGAAGCACAGAGGGAAAAAGACACACGGATCTCAAAGAAGATGGAGACCATGGGCATCTAC
TTTGCAACACCAGAATGGGTAGCACTCAATGGGCACCGAGGGCCAAGCCCCGGCCAGCTAAAGTACTGGCAG
AACACACGAGAAATACCGGACCCAAACGAGGACTATCTAGACTACGTGCATGCAGAGAAGAGCCGGTTGGCA
TCAGAAGAACAAATCCTAAGGGCAGCTACGTCGATCTACGGGCTCCAGGACAGGCAGAGCCACCCCAAGCT
TTCATAGACGAAGTTGCCAAAGTCTATGAAATCAACCATGGACGTGGCCCAAACCAAGAACAGATGAAAGAT
CTGCTCTTGACTGCGATGGAGATGAAGCATCGCAATCCCAGGCGGGCTCTACCAAAGCCCAAGCCAAAACCC
AATGCTCCAACACAGAGACCCCCTGGTCGGCTGGGCCGCTGGATCAGGACCGTCTCTGATGAGGACCTTGAG
TGAGGCTCCTGGGAGTCTCCCGACACCACCCGCGCAGGTGTGGACACCAATTCGGCCTTACAACCCAAATTG
GATCCGTTCGCGGGTCCCCT 3258
```

Fig. 1A - Segment A of IBDV V903/78 (SEQ. ID. NO: 1)

1 GGATACGATGGGTTTGACCCTCAGGGAGTCACGAATTAACATGGCTACTAGGGGCGATACCCGCCGCTGGCTGC
CACGTTAGTGGCTCCTCTTCTTGATGATTCTGCCACCATGAGTGACATTTTCAACAGTCCACAGGCGCGAAGCACG
ATCTCAGCAGCGTTCGGCATAAAGCCTACTGCTGGACAAGACGTGGAAGAACTCTTGATCCCTAAAGTTTGGGTGC
CACCTGAGGATCCGCTTGCCAGCCCTAGTCGACTGGCAAAGTTCCTCAGAGAGAACGGCTACAAAGTTTTGCAGCC
ACGGTCTCTGCCCGAGAATGAGGAGTATGAGACCGACCAAATACTCCCAGACTTAGCATGGATGCGACAGATAGAA
GGGGCTGTTTTAAAACCCACTCTATCTCTCCCTATTGGAGATCAGGAGTACTTCCCAAAGTACTACCCAACACATC
GCCCTAGCAAGGAGAAGCCCAATGCGTACCCGCCAGACATCGCACTACTCAAGCAGATGATTTACCTGTTTCTCCA
GGTTCCAGAGGCCAACGAGGGCCTAAAGGATGAAGTAACCCTCTTGACCCAAAACATAAGGGACAAGGCCTATGGA
AGTGGGACCTACATGGGACAAGCAACTCGACTTGTGGCCATGAAGGAGGTCGCCACTGGAAGAAACCCAAACAAGG
ATCCTCTAAAGCTTGGGTACACTTTTGAGAGCATCGCGCAGCTACTTGACATCACACTACCGGTAGGCCCACCCGG
TGAGGATGACAAGCCCTGGGTGCCACTCACAAGAGTGCCGTCACGGATGTTGGTGCTGACGGGAGACGTAGATGGC
GACTTTGAGGTTGAAGATTACCTTCCCAAAATCAACCTCAAGTCATCAAGTGGACTACCATATGTAGGTCGCACCA
AAGGAGAGACAATTGGCGAGATGATAGCTATCTCAAACCAGTTTCTCAGAGAGCTATCAACACTGTTGAAGCAAGG
TGCAGGGACAAAGGGGTCAAACAAGAAGAAGCTACTCAGCATGTTAAGTGACTATTGGTACTTATCATGCGGGCTT
TTGTTTCCAAAGGCTGAAAGGTACGACAAAAGCACATGGCTCACCAAGACCCGGAACATATGGTCAGCTCCATCCC
CAACACACCTCATGATCTCTATGATCACCTGGCCCGTGATGTCCAACAGCCCAAATAACGTGTTGAACATTGAAGG
GTGTCCATCACTCTACAAATTCAACCCGTTCAGAGGAGGGTTGAACAGGATCGTCGAGTGGATATTGGCCCCGGAA
GAACCCAAGGCTCTTGTATATGCGGACAACATATACATTGTCCACTCAAACACGTGGTACTCAATTGACCTAGAGA
AGGGTGAGGCAAACTGCACTCGCCAACACATGCAAGCCGCAATGTACTACATACTCACCAGAGGGTGGTCAGACAA
CGGCGACCCAATGTTCAATCAAACATGGGCCACCTTTGCCATGAACATTGCCCCTGCTCTAGTGGTGGACTCATCG
TGCCTGATAATGAACCTGCAAATTAAGACCTATGGTCAAGGCAGCGGGAATGCAGCCACGTTCATCAACAACCACC
TCTTGAGCACGCTAGTGCTTGACCAGTGGAACCTGATGAGACAGCCCAGACCAGACAGCGAGGAGTTCAAATCAAT
TGAGGACAAGCTAGGTATCAACTTTAAGATTGAGAGGTCCATTGATGATATCAGGGGCAAGCTGAGACAGCTTGTC
CTCCTTGCACAACCAGGGTACCTGAGTGGGGGGGTTGAACCAGAACAATCCAGCCCAACTGTTGAGCTTGACCTAC
TAGGGTGGTCAGCTACATACAGCAAAGATCTCGGGATCTATGTGCCGGTGCTTGACAAGGAACGCCTATTTTGTTC
TGCTGCGTATCCCAAGGGAGTAGAGAACAAGAGTCTCAAATCCAAAGTCGGGATCGAGCAGGCATACAAGGTAGTC
AGGTATGAGGCGTTGAGGTTGGTAGGTGGTTGGAACTACCCACTCCTGAACAAAGCCTGCAAGAATAACGCAGGCG
CCGCTCGGCGGCATCTGGAGGCCAAGGGGTTCCCACTCGACGAGTTCCTAGCCGAGTGGTCTGAGCTGTCAGAGTT
CGGTGAGGCCTTCGAAGGCTTCAATATCAAGCTGACCGTAACATCTGAGAGCCTAGCCGAACTGAACAAGCCAGTA
CCCCCCAAGCCCCCAAATGTCAACAGACCAGTCAACACTGGGGGACTCAAGGCAGTCAGCAACGCCCTCAAGACCG
GTCGGTACAGGAACGAAGCCGGACTGAGTGGTCTCGTCCTTCTAGCCACAGCAAGAAGCCGTCTGCAAGATGCAGT
TAAGGCCAAGGCAGAAGCCGAGAAACTCCACAAGTCCAAGCCAGACGACCCCGATGCAGACTGGTTCGAAAGATCA
GAAACTCTGTCAGACCTTCTGGAGAAAGCCGACATCGCCAGCAAGGTCGCCCACTCAGCACTCGTGGAAACAAGCG
ACGCTCTTGAAGCAGTTCAGTCGACTTCCGTGTACACCCCAAGTACCCAGAAGTCAAGAACCCACAGACCGCCTC
CAACCCCGTTGTTGGGCTCCACCTGCCCGCCAAGAGAGCCACCGGTGTCCAGGCCGCTCTTCTCGGAGCAGGAACG
AGCAGACCAATGGGGATGGAGGCCCCAACACGGTCCAAGAACGCCGTGAAAATGGCCAAACGGCGGCAACGCCAAA
AGGAGAGCCGCTAACAGCCATGATGGGAACCACTCAAGAAGAGGACACTAATCCCAGACCCCGTATCCCCGGCCTT
CGCCTGCGGGGGCCCCC 2827

Fig. 1B - Segment B of IBDV V903/78 (SEQ. ID. NO: 2)

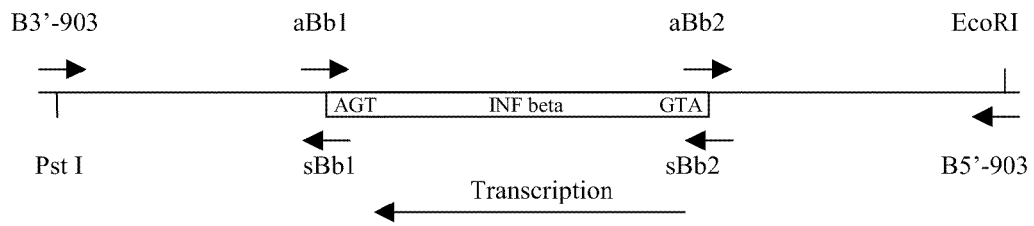
Fig. 5
pC903-INFgP
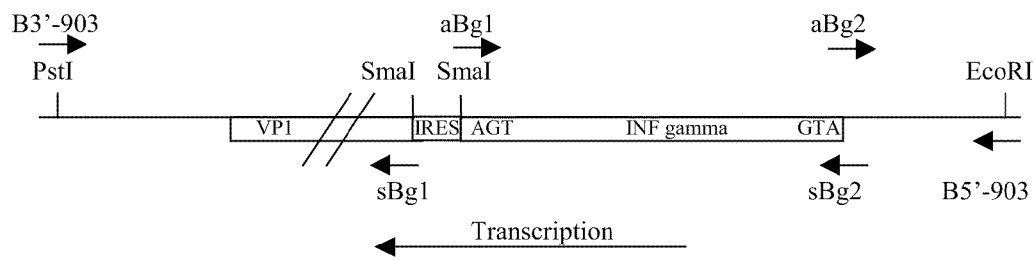
pC903-INFgD
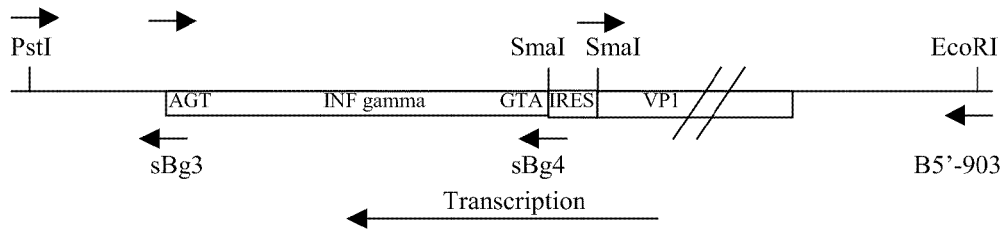
Fig. 6 pA903Afl
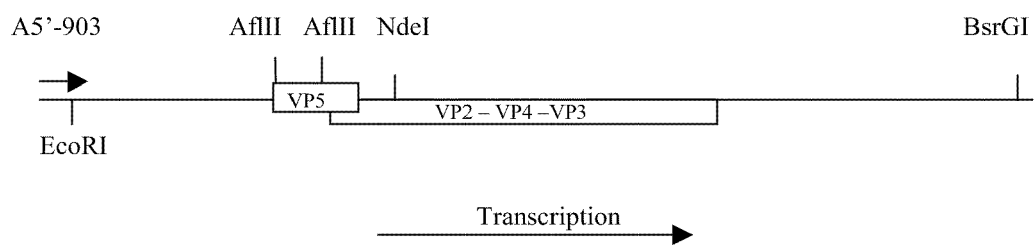
pC903-INFa
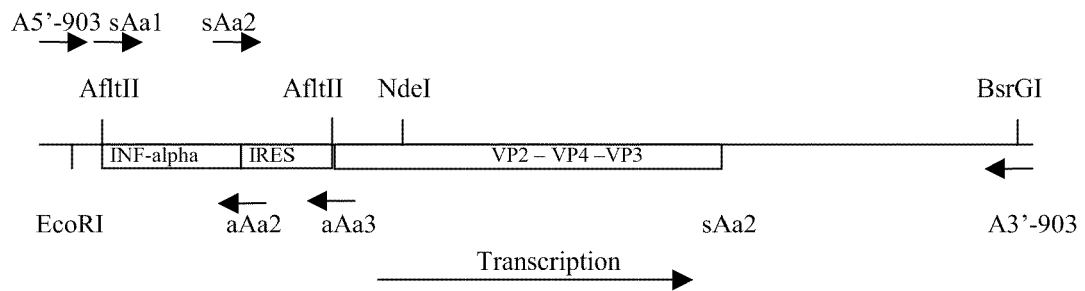
Fig. 7

SEQUENCE LISTING

```
<160> NUMBER OF SEQ ID NOS: 10

<210> SEQ ID NO 1
<211> LENGTH: 3258
<212> TYPE: DNA
<213> ORGANISM: Infectious bursal disease virus

<400> SEQUENCE: 1
ggatacgatc ggtctgaccc cggggagtc acccgggac aggccgtcaa ggctttgttc      60
caggatggaa ctcctccttc tacaacgcta tcattgatgg tcagtagaga tcagacaaac    120
gatcgcagcg atgacaaacc tgcaagatca aacccaacag attgttccgt tcatacggag    180
ccttctgatg ccaacaaccg gaccggcgtc cattccggac gacaccctgg agaagcacac    240
tctcaggtca gagacctcga cctacaattt gactgtgggg gacacagggt cagggctaat    300 tgtcttttc cctggattcc ctggctcaat tgtgggtgct cactacacac tgcagagcaa    360
tgggaactac aagttcgatc agatgctcct gactgcccag aacctaccgg ccagttacaa    420
ctactgcagg ctagtgagtc ggagtctcac agtgaggtca agcacacttc ctggtggcgt    480
ttatgcacta aacggcacca taaacgccgt gaccttccaa ggaagcctga gtgaactgac    540
agatgttagc tacaatgggt tgatgtctgc aacagccaac atcaacgaca aaattgggaa    600
cgtcctagta ggggaagggg tcaccgtcct cagcttaccc acatcatatg atcttggta     660 tgtgaggctt ggtgacccca ttcccgcaat agggcttgac ccaaaaatgg tagccacatg    720
tgacagcagt gacaggccca gagtctacac cataactgca gccgatgatt accaattctc    780
atcacagtac caaccaggtg gggtaacaat cacactgttc tcagccaaca ttgatgccat    840
cacaagcctc agcgttgggg gagagctcgt gtttcaaaca agcgtccacg gcattgtact    900
gggcgccacc atctacctca taggctttga tgggacagcg gtaatcacca gggctgtggc    960
cgcaaacaat gggctgacga ccggcaccga caacttatg ccattcaatc ttgtgattcc   1020
aacaaacgag ataacccagc caatcacatc catcaaactg gagatagtga cctccaaaag   1080
tggtggtcag gcaggggatc agatgtcatg gtcggcaaga gggagcctag cagtgacgat   1140
ccatggtggc aactatccag gggccctccg tcccgtcacg ctagtggcct acgaaagagt   1200
ggcaacagga tccgtcgtta cggtcgctgg ggtgagcaac ttcgagctga tcccaaatcc   1260
tgaactagca aagaacctgg ttacagaata cggccgattt gacccaggag ccatgaacta   1320
cacaaaattg atactgagtg agagggaccg tcttggcatc aagaccgtct ggccaacaag   1380
ggagtacact gactttcgtg aatacttcat ggaggtggcc gacctcaact ctcccctgaa   1440
gattgcagga gccttcggct tcaaagacat aatccgggcc ataaggagga tagctgtgcc   1500
ggtggtctcc acattgttcc cacctgccgc tccctagcc catgcaattg gggaaggtgt   1560
agactacctg ctgggcgatg aggcacaggc tgcttcagga actgctcgag ccgcgtcagg   1620
aaaagcaaga gctgcctcag gccgcataag gcagctgact ctcgccgccg acaagggta   1680 cgaggtagtc gcgaatctat tccaggtgcc ccagaatccc gtagtcgacg ggattcttgc   1740
ttcacctggg gtactccgcg gtgcacacaa cctcgactgc gtgttaagag agggtgccac   1800
gctattccct gtggttatta cgacagtgga agacgccatg acacccaaag cattgaacag   1860
```

```
caaaatgttt gctgtcattg aaggcgtgcg agaagacctc caacctccat ctcaaagagg    1920
atccttcata cgaactctct ctggacacag agtctatgga tatgctccag atggggtact    1980
tccactggag actgggagag actacaccgt tgtcccaata tgatgatgtct ggacgacag    2040 cattatgctg tccaaagatc ccatacctcc tattgtggga aacagtggaa atctagccat    2100
agcttacatg gatgtgtttc gacccaaagt cccaatccat gtggctatga cgggagccct    2160
caatgcttgt ggcgagattg agaaagtaag ctttagaagc accaagctcg ccactgcaca    2220
ccgacttggc cttaagttgg ctggtcccgg agcattcgat gtaaacaccg ggcccaactg    2280
ggcaacgttc atcaaacgtt tccctcacaa tccacgcgac tgggacaggc tcccctacct    2340
caacctacca taccttccac ccaatgcagg acgccagtac caccttgcca tggctgcatc    2400
agagttcaaa gagaccccg aactcgagag tgccgtcaga gcaatggaag cagcagccaa    2460
cgtggaccca ctattccaat ctgcactcag tgtgttcatg tggctggaag agaatgggat    2520
tgtgactgac atggccaact tcgcactcag cgacccgaac gcccatcgga tgcgaaattt    2580
tcttgcaaac gcaccacaag caggcagcaa gtcgcaaagg gccaagtacg ggacagcagg    2640
ctacggagtg gaggctcggg gccccacacc agaggaagca cagagggaaa aagacacacg    2700
gatctcaaag aagatggaga ccatgggcat ctactttgca acaccagaat gggtagcact    2760
caatgggcac cgagggccaa gccccggcca gctaaagtac tggcagaaca cacgagaaat    2820
accggaccca aacgaggact atctagacta cgtgcatgca gagaagagcc ggttggcatc    2880
agaagaacaa atcctaaggg cagctacgtc gatctacggg gctccaggac aggcagagcc    2940
accccaagct ttcatagacg aagttgccaa agtctatgaa atcaaccatg gacgtggccc    3000
aaaccaagaa cagatgaaag atctgctctt gactgcgatg gagatgaagc atcgcaatcc    3060
caggcgggct ctaccaaagc ccaagccaaa acccaatgct ccaacacaga gacccctgg    3120 tcggctgggc cgctggatca ggaccgtctc tgatgaggac cttgagtgag gctcctggga    3180
gtctcccgac accacccgcg caggtgtgga caccaattcg gccttacaac ccaaattgga    3240
tccgttcgcg ggtcccct                                                  3258
```

<210> SEQ ID NO 2
<211> LENGTH: 2827
<212> TYPE: DNA
<213> ORGANISM: Infectious bursal disease virus

<400> SEQUENCE: 2

```
ggatacgatg ggtttgaccc tcagggagtc acgaattaac atggctacta ggggcgatac     60
ccgccgctgg ctgccacgtt agtggctcct cttcttgatg attctgccac catgagtgac    120
attttcaaca gtccacaggc gcgaagcacg atctcagcag cgttcggcat aaagcctact    180
gctggacaag acgtggaaga actcttgatc cctaaagttt gggtgccacc tgaggatccg    240
cttgccagcc ctagtcgact ggcaaagttc ctcagagaga acggctacaa agttttgcag    300
ccacggtctc tgcccgagaa tgaggagtat gagaccgacc aaatactccc agacttagca    360
tggatgcgac agatagaagg ggctgtttta aaacccactc tatctctccc tattggagat    420
caggagtact tcccaaagta ctacccaaca catcgcccta gcaaggagaa gcccaatgcg    480
tacccgccac acatcgcact actcaagcag atgatttacc tgtttctcca ggttccagag    540
gccaacgagg gcctaaagga tgaagtaacc ctcttgaccc aaaacataag ggacaaggcc    600 tatgaagtg gaacctacat gggacaagca actcgacttg tggccatgaa ggaggtcgcc    660
actggaagaa acccaaacaa ggatcctcta aagcttgggt acacttttga gagcatcgcg    720
```

```
cagctacttg acatcacact accggtaggc ccacccggtg aggatgacaa gccctgggtg      780
ccactcacaa gagtgccgtc acggatgttg gtgctgacgg gagacgtaga tggcgacttt      840
gaggttgaag attaccttcc caaaatcaac ctcaagtcat caagtggact accatatgta      900
ggtcgcacca aggagagac aattggcgag atgatagcta tctcaaacca gtttctcaga       960
gagctatcaa cactgttgaa gcaaggtgca gggacaaagg ggtcaaacaa gaagaagcta     1020
ctcagcatgt taagtgacta ttggtactta tcatgcgggc ttttgtttcc aaaggctgaa     1080
aggtacgaca aaagcacatg gctcaccaag acccggaaca tatggtcagc tccatcccca     1140
acacacctca tgatctctat gatcacctgg cccgtgatgt ccaacagccc aaataacgtg     1200
ttgaacattg aagggtgtcc atcactctac aaattcaacc cgttcagagg agggttgaac     1260
aggatcgtcg agtggatatt ggccccggaa gaacccaagg ctcttgtata tgcggacaac     1320
atatacattg tccactcaaa cacgtggtac tcaattgacc tagagaaggg tgaggcaaac     1380
tgcactcgcc aacacatgca agccgcaatg tactacatac tcaccagagg gtggtcagac     1440
aacggcgacc caatgttcaa tcaaacatgg gccacctttg ccatgaacat tgcccctgct     1500
ctagtggtgg actcatcgtg cctgataatg aacctgcaaa ttaagaccta tggtcaaggc     1560
agcgggaatg cagccacgtt catcaacaac cacctcttga gcacgctagt gcttgaccag     1620
tggaacctga tgagacagcc cagaccagac agcgaggagt tcaaatcaat tgaggacaag     1680
ctaggtatca actttaagat tgagaggtcc attgatgata tcaggggcaa gctgagacag     1740
cttgtcctcc ttgcacaacc agggtacctg agtgggggg ttgaaccaga acaatccagc     1800
ccaactgttg agcttgacct actagggtgg tcagctacat acagcaaaga tctcgggatc     1860
tatgtgccgg tgcttgacaa ggaacgccta ttttgttctg ctgcgtatcc caagggagta     1920
gagaacaaga gtctcaaatc caaagtcggg atcgagcagg catacaaggt agtcaggtat     1980
gaggcgttga ggttggtagg tggttggaac tacccactcc tgaacaaagc ctgcaagaat     2040
aacgcaggcg ccgctcggcg gcatctggag gccaaggggt tcccactcga cgagttccta     2100
gccgagtggt ctgagctgtc agagttcggt gaggccttcg aaggcttcaa tatcaagctg     2160
accgtaacat ctgagagcct agccgaactg aacaagccag tacccccaa gcccccaaat     2220 gtcaacagac cagtcaacac tggggggactc aaggcagtca gcaacgccct caagaccggt     2280
cggtacagga acgaagccgg actgagtggt ctcgtccttc tagccacagc aagaagccgt     2340
ctgcaagatg cagttaaggc caaggcagaa gccgagaaac tccacaagtc caagccagac     2400
gaccccgatg cagactggtt cgaaagatca gaaactctgt cagaccttct ggagaaagcc     2460
gacatcgcca gcaaggtcgc ccactcagca ctcgtggaaa caagcgacgc tcttgaagca     2520
gttcagtcga cttccgtgta cacccccaag tacccagaag tcaagaaccc acagaccgcc     2580
tccaaccccg ttgttgggct ccacctgccc gccaagagag ccaccggtgt ccaggccgct     2640
cttctcggag caggaacgag cagaccaatg gggatggagg ccccaacacg gtccaagaac     2700
gccgtgaaaa tggccaaacg gcggcaacgc caaaaggaga gccgctaaca gccatgatgg     2760
gaaccactca agaagaggac actaatccca gaccccgtat ccccggcctt cgcctgcggg     2820
ggccccc                                                              2827
```

<210> SEQ ID NO 3
<211> LENGTH: 19
<212> TYPE: DNA
<213> ORGANISM: Artificial
<220> FEATURE:
<223> OTHER INFORMATION: Primer

```
<400> SEQUENCE: 3
ctcaagagat tcctcagcc                                              19

<210> SEQ ID NO 4
<211> LENGTH: 19
<212> TYPE: DNA
<213> ORGANISM: Artificial
<220> FEATURE:
<223> OTHER INFORMATION: Primer

<400> SEQUENCE: 4
gtcataccat tctcctact                                              19

<210> SEQ ID NO 5
<211> LENGTH: 40
<212> TYPE: DNA
<213> ORGANISM: Artificial
<220> FEATURE:
<223> OTHER INFORMATION: primer

<400> SEQUENCE: 5
ggttcccatc atggctgtta ctgggatgct cttcgacctc                       40

<210> SEQ ID NO 6
<211> LENGTH: 45
<212> TYPE: DNA
<213> ORGANISM: Artificial
<220> FEATURE:
<223> OTHER INFORMATION: Primer

<400> SEQUENCE: 6
cctcttcttg atgattctgc caccatgtta attctctcgg aaacg                 45

<210> SEQ ID NO 7
<211> LENGTH: 44
<212> TYPE: DNA
<213> ORGANISM: Artificial
<220> FEATURE:
<223> OTHER INFORMATION: Primer

<400> SEQUENCE: 7
agagaattct aatacgactc actataggat acgatgggtc tgac                  44

<210> SEQ ID NO 8
<211> LENGTH: 45
<212> TYPE: DNA
<213> ORGANISM: Artificial
<220> FEATURE:
<223> OTHER INFORMATION: Primer

<400> SEQUENCE: 8
cgtttccgag agaattaaca tggtggcaga atcatcaaga agagg                 45

<210> SEQ ID NO 9
<211> LENGTH: 33
<212> TYPE: DNA
<213> ORGANISM: Artificial
<220> FEATURE:
<223> OTHER INFORMATION: Primer

<400> SEQUENCE: 9
cgatctgctg caggggggccc ccgcaggcga agg                             33

<210> SEQ ID NO 10
<211> LENGTH: 40
```

```
<212> TYPE: DNA
<213> ORGANISM: Artificial
<220> FEATURE:
<223> OTHER INFORMATION: Primer

<400> SEQUENCE: 10
gaggtcgaag agcatcccag taacagccat gatgggaacc                             40
```

COMPOSITIONS AND METHODS FOR THE TREATMENT OF VIRAL HEPATITIS

This application is a continuation-in-part of International Application PCT/IB2007/054742, filed Nov. 22, 2007, and claims priority to Hungarian Application P0600894, filed Dec. 1, 2006, the entire disclosures of which are incorporated by reference herein.

TECHNICAL FIELD OF THE INVENTION

This invention pertains to a novel attenuated, viral replication inhibitory strain of Infectious Bursal Disease Virus (IBDV) designated V903/78 suitable for harmless propagation in human liver cells, and compositions and methods comprising the same for modulating viral liver disease in a mammal, as well as recombinant IBDV vectors comprising the said IBDV strain and uses thereof.

BACKGROUND OF THE INVENTION

When hepatitis B, C viruses (HBV and HCV respectively) persist in a chronic carrier state, they serve as a reservoir for infection and give rise to chronic hepatitis and cirrhosis that usually progress to hepatocellular carcinoma, one of the most common malignant tumors with an extremely poor prognosis. Currently approved treatments for chronic hepatitis B—interferon, lamivudin and adefovir—are limited by low rates of sustained response, side effects, or drug resistance. Managing patients with HCV infection consists primarily of antiviral treatment, currently with peginterferon and ribavirin.

IBDV has a worldwide distribution and can cause considerable damage to the poultry industry. IBDV is the causative agent of acute or immunosuppressive disease in chickens. Some zoonotic diseases are of continuing concern, however, IBDV is not known to be a hazard in transmitting to other species despite its worldwide distribution in the domestic fowl (Kibenge et al., 1988a); (Pedersden et al., 1990). IBDV is known to exert an inhibitory effect on the replication of hepatitis A virus in monkeys (Csatary et al., 1984). A bursa virus superinfection strategy has been tested for the treatment of acute B and C viral hepatitis in patients (Csatary et al., 1998). The use of IBDV as therapeutic agent in patients suffering from chronic hepatitis infections has also been reported (Bakacs and Mehrishi, 2002); (Csatary et al., 1999).

Given the hurdles associated with the development of anti HCV and HBV agents, there remains a need for improved therapy for both acute and chronic viral liver infections. This can be achieved by the use of IBDV vectors that have great flexibility in their construction and use, and can provide greater success in the treatment of viral liver diseases. An IBDV vector that can replicate in human liver cells without causing detrimental effects to them would be ideal. The present invention provides such vectors, and therapeutic methods involving the use of such vectors.

SUMMARY OF THE INVENTION

The present invention relates to an attenuated clonal, viral replication inhibitory strain of Infectious Bursal Disease Virus (IBDV) comprising the RNA nucleotide sequence of the complete virus designated IBDV V903/78 as depicted in SEQ. ID. NO: 1 and 2 or a functionally equivalent tissue culture adapted derivative thereof, which can be grown in the HepG2 human liver cell line without causing detrimental effects to the cells. Advantageously said IBDV strain can be produced at least to $10^{7.5}/0.1$ ml $TCID_{50}$ titre. The invention also provides a recombinant attenuated IBDV vector comprising the nucleotide sequence of the said IBDV strain and further comprising sequence elements for the inclusion and/or expression of exogenous nucleic acid sequences. These exogenous nucleic acid sequences can enhance the therapeutic effects of the said IBDV vector. In one preferred embodiment of the invention the exogenous nucleic acid sequence encodes a cytokine. The preferred cytokine encoded belongs to the family of interferons.

The present invention also provides pharmaceutical compositions comprising, said viral replication inhibitory strain of IBDV or said IBDV vector and a suitable carrier or excipient. In one preferred embodiment the pharmaceutical composition comprises $10^{5.0}$-$10^{8.0}$ 50% tissue culture infecting dose ($TCID_{50}$) per unit dose or, more advantageously, $10^{6.3}$-$10^{7.0}$ $TCID_{50}$ per unit dose.

The present invention provides a viral replication inhibitory strain of IBDV or an IBDV vector or a composition for use in therapy and in one preferred embodiment for use in the treatment or prevention of viral infections, preferably hepatitis.

The present invention concerns methods for treating viral hepatitis in a patient comprising administering to the patient a therapeutically effective amount of said pharmaceutical composition. In one preferred embodiment the step of administering is selected from oral, buccal, intranasal or anal administration.

The present invention further concerns methods for treating patients chronically infected with hepatitis B or C virus respectively and displaying clinical indications of advanced decompensated hepatitis by administering pharmacologically effective amount of the said live, attenuated IBDV strain or IBDV vector.

The present invention further concerns a method of treating individuals chronically infected with hepatitis B or C virus respectively but displaying no clinical indications of hepatitis (virus carriers) by administering pharmacologically effective amount of said live, attenuated IBDV strain or IBDV vector.

Furthermore the present invention relates to a system comprising:
(i) a deficient IBDV vector as defined above, and
(ii) a cell line that expresses the missing function of said vector.

According to a preferred embodiment in said system said IBDV vector comprises an IBDV genome having a deficiency in one or more essential gene functions in either or both of the VP1 region and the VP2 region of the IBDV genome. According to a still further preferred embodiment of the present invention said IBDV vector is deficient in RNA-polymerase expression and/or in the expression of other genes that are essential for the propagation of said IBDV vector.

DETAILED DESCRIPTION OF THE INVENTION

Definitions

By the expression "viral replication inhibitory strain" we mean an IBDV strain that efficiently limits the replication of a different virus, preferably a hepatitis B or hepatitis C virus, present in the same animal.

Generally an "attenuated strain" is a strain that has been altered to exhibit diminished virulence. In the case of the IBDV strain of the invention this means that it does not induce disease in specific pathogen free (SPF) chickens following artificial infection.

A "functionally equivalent" derivative of the IBDV strain of the invention, as used herein, is a derivative which retains its capability of inhibiting replication of a co-existing virus (preferably a hepatitis B or hepatitis C virus) and of being propagated in the HepG2 (ATCC Number HB-8065) human liver cell line without causing detrimental effects to the cells.

The present invention provides an apathogenic, attenuated avian virus, IBDV, as antiviral agent. IBDV belongs to the genus Avibirnavirus and is a member of the family Birnaviridae. The Birnaviridae family is known to have very narrow species limits. It was therefore quite unexpected that V903/78 was able to replicate in the human hepatoma cell line, which is separated by several hundred million years in evolution from the birds. Furthermore, it is very important to note that the IBDV replication was not associated with cytopathic effects in the HepG2 cells. Therefore, this human cell line can be used for model studies of viral interference between V903/78 virus and other viruses. IBDV remains infective at pH 2.0 and can be produced in primary chicken cell or VERO cell cultures that have been certified for other vaccines. The VERO epithelial cell line was established by Y. Yasumura and Y. Kawakita in 1962 at the Chiba University in Chiba, Japan. The tissue from which the line was derived was obtained from the kidney of a healthy adult African green monkey. VERO cells are commercially available and are widely used in transfections and vaccine production (ATCC Number CCL-81).

IBDV Genome

IBDV is a non-enveloped icosahedral virus particle of 60 nm in diameter, which contains two genome segments of double-stranded RNA (see FIG. 2). Genome segment A determines the bursa tropism of IBDV, whereas segment B is involved in the efficiency of viral replication. Significantly, the interaction of the two segments, the polymerase (segment B) with the structural protein VP3 (segment A) are necessary for efficient virus formation and replication (Zierenberg et al., 2004). The larger segment A encodes a 110 kDa precursor protein in a single large open reading frame (ORF), which is cleaved by autoproteolysis to yield mature VP2, VP3 and VP4 proteins. VP2 is the major host-protective immunogen of IBDV. The smaller segment B encodes VP1, a 97 kDa protein having RNA-dependent RNA polymerase activity. IBDV infects the precursors of antibody-producing B cells in the bursa of fabricius, which can cause immunosuppression and mortality in young chickens. Studies have shown that virulent strains of IBDV lose their virulence potential after serial passage in non-B lymphoid chicken cells. Comparison of the deduced amino acid sequences of the virulent and attenuated strains shows specific amino acid substitution within the hypervariable region of the VP2 protein.

Several quasispecies of infectious bursal disease virus vaccine and wild-type strains also were identified using real-time RT-PCR at a region of the viral genome known for sequence variability (Jackwood and Sommer, 2002). Significantly, Jackwood and Sommer, 2002 provide evidence that commercial IBDV vaccines are contaminated by mutant quasispecies. Furthermore, the authors argue that quasispecies cloud lead to chicken vaccines that have a better antigenic fitness and thus afford a broader cross protection for wild type strains which is the prevailing opinion. However, these types of undefined vaccine compositions would be unacceptable for human use, as regulatory agencies require a well well-defined homogeneous product. The instant invention solves this problem by cloning the IBDV V903/78 variant that can be produced as a homogeneous contamination free product either as the cloned derivative of the original virus or as a recombinant vector incorporating exogenous nucleotide sequences or expressing exogenous genes from its genome.

Molecular detection of IBDVs makes use of the reverse transcriptase/polymerase chain reaction (RT-PCR) to amplify the viral genome. Most assays have directed the RT-PCR to amplify the hypervariable region of the IBDV VP2 gene. This region of the VP2 gene is thought to be responsible for phenotypic differences among IBDV strains. Amplification of this region by RT-PCR and sequencing the PCR product can be used to assess the nucleotide differences among IBDV strains. Studies have shown that virulent strains of IBDV lose their virulent potential after serial passage in non-B lymphoid chicken cells or Vero cells. Comparison of the deduced amino acid sequences of the virulent and attenuated strains show specific amino acid substitution within the hypervariable region of the VP2 protein (Kwon H M and Kim S J, 2004). Using sequencing analysis, the passaged IBDVs had amino acid changes at positions 253, 279 and 284 which were commonly found in the attenuated IBDV strains. Two serines in the serine-rich heptapeptide (residue 326-332, (numbered by Bayliss et al., 1990) were substituted into other amino acids which were similar to the IBDV vaccine strains. Bayliss et al., 1990, observed that any changes in pathogenicity, between two strains, caused by differences in the proteins encoded by segment A must be due to five amino acid changes in VP2. Lim et al., 1999, provided the strongest evidence that only 2 amino acid change in the VP2 region can completely modify the virus properties. A very virulent IBDV strain was amplified into cDNAs by reverse transcription-PCR. The full-length cDNAs were sequenced and subcloned into a eukaryotic expression vector, from which point mutations were introduced into the VP2 region by site-directed mutagenesis. Substitution of amino acid residues 279 (Asp3Asn) and 284 (Ala3Thr) of the VP2 protein yielded a recombinant virus which was able to be passaged in CEF cells, whereas the wild-type cDNAs and an amino acid substitution at residue 330 (Ser3Arg) of the VP2 protein alone did not yield viable virus. The results indicated that mutation of other viral proteins, including VP1, VP3, VP4, and VP5, was not required for CEF adaptation of the virus.

Characterization of IBDV Strain V903/78

Strain V903/78 of IBDV, the antiviral agent according to the present invention for the treatment of chronic viral hepatitis B and C infections was obtained from domestic poultry in Hungary in 1978. The virus strain was isolated from the bursal tissues of a 3-week-old healthy broiler chicken by inoculation of 11-day-old embryonated specific pathogen free (SPF) eggs. The virus grown in the embryonated eggs was adapted to VERO cell culture. After 16 passages in the cell line, the strain was plaque-purified once and a stock of virus designated as V903/78 passage 19 was produced for genomic characterization. Said strain does not induce disease in SPF chickens following artificial infection, therefore this strain can be considered attenuated. This statement is supported by sequence analysis data of the VP2 gene of the V903/78 strain, which shows the closest relationship with other tissue adapted vaccine strains (see the phylogenetic tree on FIG. 3).

The V903/78 virus stock was three times further plaque-purified and grown in VERO cell culture. This viral stock was sequenced again and was used to create the Master Seed Virus (MSV) stock. The entire nucleotide sequence of the complete virus designated IBDV V903/78 (see FIGS. 1.A and 1.B) is depicted in SEQ. ID. NO: 1 (segment A) and SEQ. ID. NO: 2 (segment B).

Recombinant Vector Constructs

The present invention also provides recombinant IBDV vectors that allow for the inclusion of exogenous nucleic acid sequences. The nucleic acid sequences are operably linked to regulatory sequences necessary for expression of protein coding or non-coding sequences that enhance the therapeutic effects of the IBDV vector.

It is explicitly to be understood that any exogenous polypeptides expressed from the vector, which increases the viral replication inhibitory activity of the intact virus, is within the scope of the present invention. Accordingly the polynucleotides encoding any such protein or protein fragment are within the scope of the invention.

Synthetic transcripts of double-stranded Birnavirus genomes are infectious when constructed from cRNA (Mundt and Vakharia, 1996). Method for generating birnavirus from synthetic RNA transcripts is further described in U.S. Pat. No. 5,871,744. A method for generating recombinant birnavirus from synthetic RNA transcripts was also described in U.S. Pat. No. 6,596,280. Efficient rescue of infectious bursal disease virus from cloned cDNA has also been developed (Boot et al., 2000) and the two above methods were extensively evaluated (Boot et al., 2001).

The present invention provides pharmaceutical compositions comprising at least one non-pathogenic viral replication inhibitory strain of IBDV for the treatment of viral hepatitis. Preferably, the V903/78 strain of IBDV is utilized in the treatment of viral hepatitis. Said composition further comprises suitable carriers and excipients.

Method for treating viral diseases with an attenuated strain of avian bursa virus was previously disclosed in U.S. Pat. Nos. 5,124,148; 5,215,745. The process of preparation of live, stabilized virus for the therapy of viral and malignant process was also described in U.S. Pat. No. 5,602,023.

The method of the invention for treatment of viral hepatitis, according to an embodiment of the invention, includes the step of administering to a patient a therapeutically effective amount of a composition comprising as an active ingredient the viral replication inhibitory strain of IBDV, preferably the V903/78 strain.

Transfer of the wild type virus usually takes place via the fecal-oral route. IBDV can persist in poultry houses even after thorough cleaning and disinfecting. This virus is more resistant to heat and ultraviolet light than reovirus. It is inactivated at pH 12.0, but remains infective at pH 2.0. Therefore, the composition may be administered to the patient through any suitable route, but one particularly preferred embodiment utilizes the oral route of administration.

Preferably, the compositions of the invention comprise $10^{5.0}$-$10^{8.0}$ TCID$_{50}$ per each treatment dose of the V903/78 strain or its recombinant derivatives. More preferably, the composition comprises $10^{6.3}$-$10^{7.0}$ TCID$_{50}$ per each treatment dose of the V903/78 strain or its recombinant derivatives. Information on possible formulation of the V903/78 vector can be found in U.S. Pat. Nos. 6,225,289, 6,514,943.

Thus the compositions and methods of the invention provide a treatment for viral hepatitis that does not share the risk that may be involved in the use of live pathogenic strains of viruses.

Experimental Methods Useful in the Elaboration and Quality Control of the Advantageous Embodiments of the Invention IFN-Alpha, IFN-Beta and TNF-Alpha Induction by IBDV Strain V903/78 in HepG2 Cell Line Induction of cytokines such as IFN-alpha, IFN-beta and TNF-alpha is investigated in human hepatocytes by IBDV strain V903/78 infection. HepG2 cells are infected with V903/78 virus at a multiplicity of infection (MOI) of approximately 1 to 100 plaque forming unit (pfu). Between 1 and 10 days post-infection, cytokine induction is measured from the supernatant media by ELISA measurements. The ELISA measurements performed for IFN-alpha, IFN-beta and TNF-alpha with the use of commercially available ELISA kits. The levels of cytokines present in the supernatant of infected HepG2 cells are compared to uninfected HepG2 cells. At 10 days post-infection intracellular RNA is harvested from the cells. The quantities of cytokine mRNAs are determined by RT-PCR with cytokine specific primers, and the levels of specific mRNAs are compared to uninfected HepG2 cells.

Stability of IBDV Strain V903/78 after In Vivo Oral Delivery in Mice Gut

Five 6-week-old Balb/c mice are inoculated orally with 0.1 ml of $10^{6.3}$ IBDV strain V903/78 (virus titre: $10^{6.3}$ TCID$_{50}$/0.1 ml). Next day all mice are sacrificed and samples are collected from feces. The feces are diluted into media and virus is grown on confluent adherent cell cultures of African green monkey VERO cell line. VERO cells are incubated for 5 days at 37° C. in a 5% CO$_2$ atmosphere, cultures are microscopically monitored every day for cytopathic effect (CPE) at 10, 20 and 40× magnification, and photographs are taken at the 5$^{th}$ day of culture. Cell free culture supernatants and supernatants containing lysed cells (after three freeze-thaw cycle) are taken at 24 hour intervals up to 120 hour post-inoculation. IBDV virus titre determination of samples is done by standard titration method. The presence of IBDV strain V903/78 is verified by PCR. A nested PCR method is used to amplify a 414 bp product spanning from 750 to 1163 nt (numbered by Bayliss et al., 1990), which encompasses the hypervariable region of the VP2 gene.

IFN-Alpha, IFN-Beta and TNF-Alpha Induction by IBDV Strain V903/78 in Mice Liver On day 1, five 6-week-old Balb/c mice are inoculated orally with 0.1 ml of $10^{6.3}$ IBDV strain V903/78 (virus titre: $10^{6.3}$ TCID$_{50}$/0.1 ml). On day 2 and day 3 the mice are repeatedly infected orally by the same amounts of IBDV. On day 5 all mice are sacrificed and samples are collected into liquid nitrogen for viral culture and histological studies from lymph nodes, spleen, liver, lung, kidneys, intestine, Peyer patches, thymus. Liver and intestine samples are also collected for ELISA measurements. The tissues are ground and ELISA measurements performed on the tissue lysates for IFN-alpha, IFN-beta and TNF-alpha with the use of commercially available ELISA kits. The levels of cytokines in infected animal tissues are compared to uninfected animal tissue.

Viral Interference Between V903/78 Virus and DHBV (Duck Hepatitis Virus) In Vitro in HepG2 Cells To demonstrate that IBDV inhibits HBV/HCV replication directly by viral interference, superinfection is carried out such that HepG2 cells are transfected with an infectious DHBV plasmid and then superinfected with V903/78 virus. Superinfection is carried out by transfecting HepG2 cells with closed circular DHBV DNA as described by Galle et al., J Virol (1988) 62:1736-40. Circular DNA is prepared from plasmid pD16, which carries a full-length DHBV type 16 (DHBV-16) genome in the EcoRI site of pUC13. Full-length DHBV DNA is excised with EcoRI, circularized with T4

DNA ligase, and introduced into cells by calcium phosphate transfection. Sub-confluent HepG2 cells are passaged at a 1:5 dilution; 20 h later the medium is changed, and another 2 h later 1 ml of transfection cocktail (10 μg of DNA, 438 μl of Tris [pH 7.6], 62 μl of 2 M $CaCl_2$, 500 ml of HEPES-buffered saline [280 mM NaCl, 1.5 mM $Na_2HPO_4$, 50 mM N-2-hydroxyethylpiperazine-N'-2-ethanesulfonic acid]) is added per 75-$cm^2$ dish. After 12 h, dimethyl sulfoxide is added to a final concentration of 10%, and the cells are incubated at 37° C. for 20 min. The medium is changed afterwards. The cells are then superinfected with V903/78 virus 1, 2, 5 days later at an MOI of approximately 1 to 100 pfu. Between 6 and 10 days post-infection, intracellular viral DNA and RNA respectively are harvested, amplified by PCR and RT-PCR respectively, and analyzed for the presence of DHBV and V903/78 virus genomes to determine viral interference between the two viruses.

Viral Interference Between V903/78 Virus and its Derivatives and DHBV In Vivo in the Duck Model of HBV The avian duck hepatitis B virus model system is used for studying the clinically observed efficacy of IBDV superinfection therapy. Newborn Pekin ducklings, either congenitally infected with DHBV type 16 or uninfected, are obtained from the University of Alberta, Edmonton, Alberta, Canada. Wild-type DHBV is obtained from the serum of congenitally infected ducks. Viral titers are quantitated before and after IBDV treatment by dot blotting with plasmid standards and are expressed as viral genome equivalents (VGE). The technical details are described in the paper of Walters et al. (Walters et al., 2004).

Five newborn ducklings congenitally infected with DHBV in each of the 6 groups are inoculated orally with 0.1 ml of $10^{6.3}$ IBDV strain V903/78; 903/78INFb, 903/78INFa, 903/78INFgP and 903/78INFgD viruses (virus titre: $10^{6.3}$ $TCID_{50}$/0.1 ml). One group that is not superinfected with IBDV is used as control. Two DHBV uninfected ducklings are used as negative controls. IBDV treatment is repeated every 3 days and the health and weight of the animals are monitored. Reduction of the DHBV virus titers are monitored in the serum every ten days by PCR methodology.

Extracellular viral DNA is extracted from serum for analysis. Twenty microliters of serum is added to 80 μl of 50 mM Tris-HCl (pH 8)-150 mM NaCl-10 mM EDTA-0.1% sodium dodecyl sulfate (SDS)-800 μg of proteinase K/ml and incubated at 42° C. for a minimum of 4 h. The sample is extracted with an equal volume of phenol-chloroform. DNA is precipitated by adding a 0.1 volume of 3 M sodium acetate, 10 μg of yeast tRNA, and 2 volumes of 95% ethanol. The DNA is resuspended in 20 μl of water. Ten microliters is used for a subsequent PCR. The extracted viral DNA is amplified by PCR with Taq polymerase (Gibco BRL) according to the manufacturer's specifications, 1.5 mM $MgCl_2$, and the following primers at 0.25 μM: 5'-CTCAAGAGATTCCTCAGCC-3' (SEQ. ID. NO: 3)

and 5'-GTCATACCATTCTCCTACT-3' (SEQ. ID. NO: 4). Cycling conditions are as follows: 95° C. for 4 min; 30 cycles of 95° C. for 30 s, 50° C. for 30 s, and 72° C. for 1 min; and 72° C. for 7 min. The PCR products are separated on 1.3% agarose gels and visualized with ethidium bromide to observe the 906 bp DHBV specific products.

On day 30 post IBDV infection, all ducks are sacrificed and samples are collected into liquid nitrogen for viral culture, histological studies, PCR and ELISA for cytokines (IFN-alpha, IFN-beta, IFN-gamma and TNF-alpha) from lymph nodes, spleen, liver, lung, kidneys, intestine, Peyer patches, thymus. Reduction of the DHBV virus titers are also evaluated by DNA dot blot and quantitative PCR methodologies.

Single or Multiple Deficient Vectors and Complementing Cell Lines

For various applications the use of single or multiple deficient vectors may be highly advantageous. A deficient IBDV vector could be complemented by a cell line that expresses the missing function of the vector. An example of this would be an IBDV vector missing or having a non-functional polymerase. The smaller segment B of IBDV encodes VP1, a 97 kDa protein having RNA-dependent RNA polymerase activity. If this segment is expressed in a production cell line (e.g. VERO cells) that cell line allows the manufacture of an RNA polymerase deficient IBDV vector by complementarity (see e.g. U.S. Pat. No. 7,195,896).

It has been demonstrated that the recombinant IBDV viruses lacking VP5 can still be propagated without the need for a complementing cell line. However to dispense with other viral proteins to expand on the use of recombinant IBDV viruses, complementing cell lines would be required. Currently cell lines expressing the individual proteins are not available for such a project, although the expression of the entire segment A was attempted (Ye et al., 2007). IBDV virus is generally cultured in chicken embryo fibroblast cells, but strains of this virus can also be propagated in Vero cells. As Vero cells are easier to maintain in culture it was decided to use these as the basis for the new cell lines. In the first instance a Vero cell line expressing pVP2 (the precursor protein of VP2) was constructed. Another cell line also being constructed that is expresses the VP1 protein in a Vero cell line to be used with the system of a VP1 deficient IBDV vector.

BRIEF DESCRIPTION OF THE DRAWINGS

The present invention will be understood and appreciated more fully from the following detailed description taken in conjunction with the drawings.

FIGS. 1A and 1B depicts the complete nucleotide sequences of Segment A and Segment B, respectively, of IBDV strain V903/78 of the invention.

FIG. 5. Schematic diagram of cDNA construct and primers used for the construction of pC903-INFb plasmid.

FIG. 6. Schematic diagram of cDNA construct and primers used for the construction of pC903-INFgP (proximal) and pC903-INFgD (distal) plasmids.

FIG. 7. Schematic diagram of the pC903-AflII plasmid and the cDNA construct and primers used for the construction of the pC903-INFa plasmid.

Figures 8, 9:
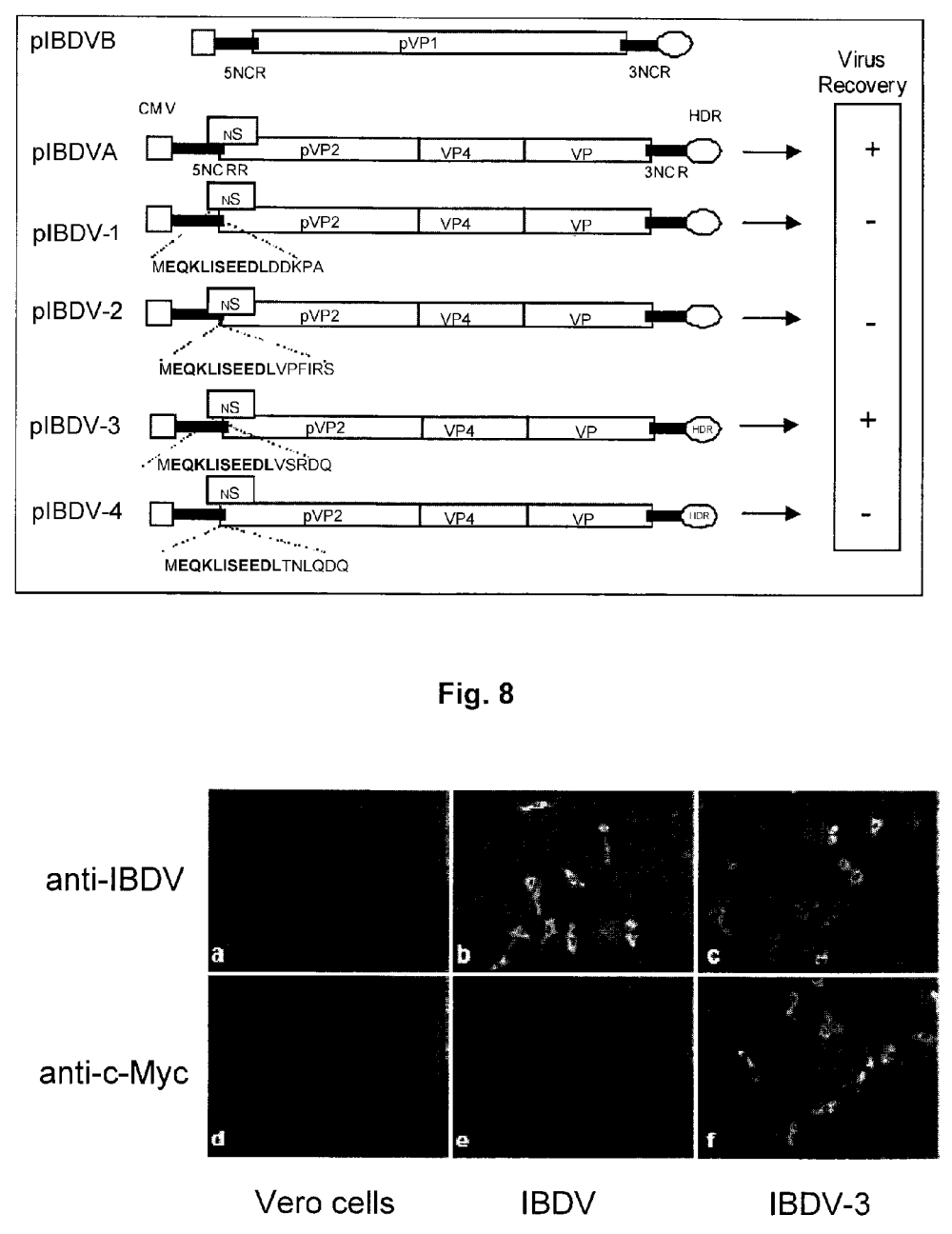

FIG. 8. Schematic representation of segment A and B of IBDV plasmids utilizing the construction system of Abdeljelil et al. 2008. Segment A was further modified to construct the plasmids with c-Myc epitope, which is shown in bold letters. IBDV-1: substitute the 5' terminal of VP5 with c-Myc; IBDV-2: substitute the 5' terminal of VP2 with c-Myc; IBDV-3: insert c-Myc at 5' terminal of VP5; IBDV-4: insert c-Myc at 5' terminal of VP2; Vero cells were transfected with segment B and different segment A construct. The virus infectivity was monitored by immunofluorescence and western blotting. The recovery of virus progeny is indicated by (+/−).

FIG. 9. Immunofluorescence assay of recombinant virus with c-Myc epitope. Vero cells were infected with IBDV and IBDV-3 virus at an MOI of 1. Uninfected Vero cells were used as negative controls (a and d). Vero cells were infected with as IBDV (b and e) and IBDV-3 (c and f) After 24 hrs post-infection, the cells were fixed and analyzed by immunofluorescence staining with rabbit anti-IBDV (a, b, and c) and c-Myc monoclonal antibody (d, e and f).

EXAMPLES

The following examples further illustrate the present invention but should not be construed as in any way limiting its scope.

Example 1

IBDV Strain V903/78 is Grown in the HepG2 Human Liver Cell Line Without Causing Detrimental Effects to the Cells Virus replication was measured in half confluent adherent cell culture of HepG2 cells. Uninfected cells were used for controls (FIG. 4A). The $TCID_{50}$ titers of IBDV V903/78 seed virus produced on HepG2 cells were $10^{5.0}/0.1$ ml on HepG2 and $10^{8.0}/0.1$ ml on chicken embryo fibroblast (CEF) cells. Importantly, the closely related IBDV strain, D78 grew only to $10^{4.35}/0.1$ ml to $10^{5.10}/0.1$ ml on CEF cells and to $10^{5.85}/0.1$ ml to $10^{7.35}/0.1$ ml on Vero cells (Kibenge et al. 1988b). $11.6 \times 10^5$ HepG2 cells were seeded into a 25 cm² tissue culture flask, which was inoculated by 1 ml of 500× diluted seed virus. HepG2 cells were incubated for 5 days at 37° C. in a 5% $CO_2$ atmosphere, cultures were microscopically monitored every day (at 10, 20 and 40× magnification), and photographs were taken at the $5^{th}$ day of culture (FIG. 4B). Following 5 days of culture, supernatants were harvested and titrated on CEF cells. The titers of harvest taken from culture inoculated at half confluence were $10^{4.7}/0.1$ ml on HepG2 and $10^{7.4}/0.1$ ml on CEF cells.

Figure 2:
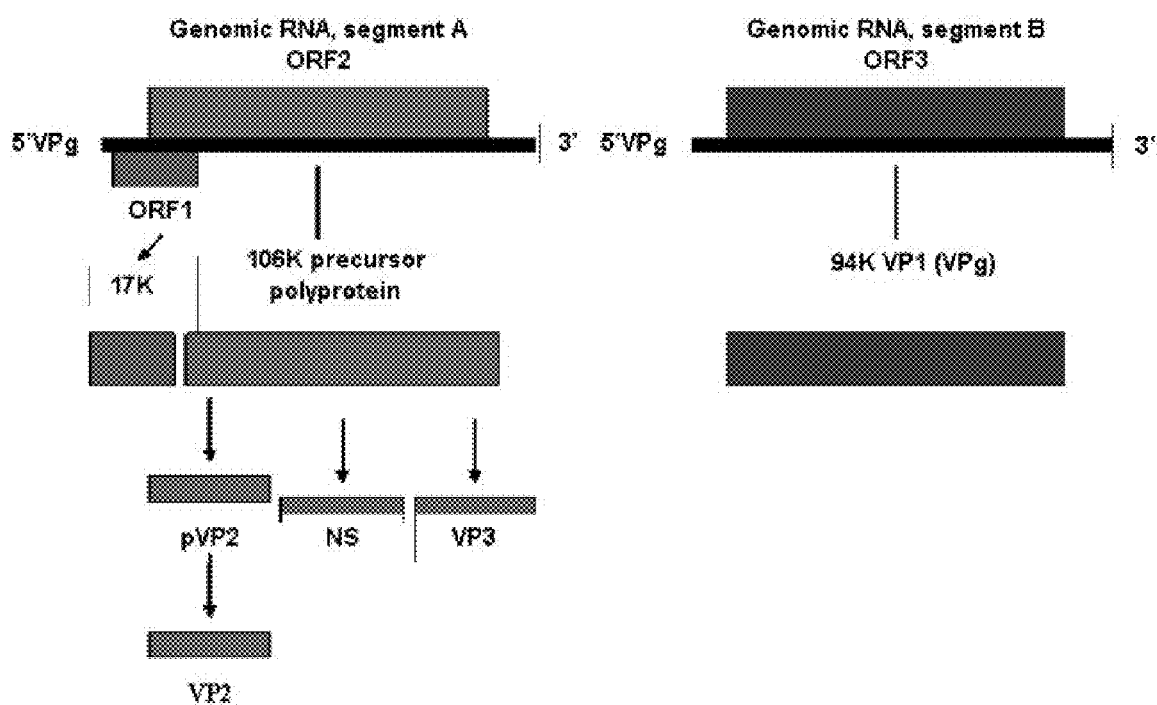
FIG. 2. The genome of IBDV consists of two segments of double-stranded RNA. The larger segment A encodes a 110 kDa precursor protein in a single large open reading frame (ORF), which is cleaved by autoproteolysis to yield mature VP2, VP3 and VP4 proteins. VP2 is the major host-protective immunogen of IBDV. The smaller segment B encodes VP1, a 97 kDa protein having RNA-dependent RNA polymerase activity.
Figure 3:
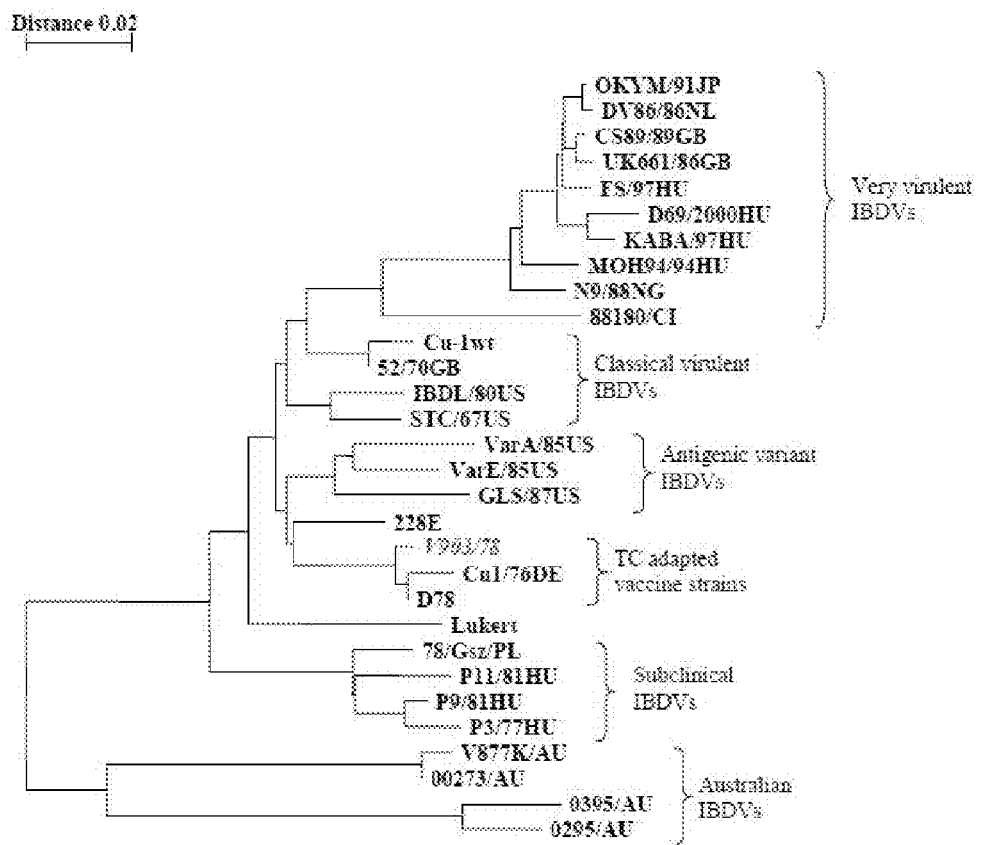
FIG. 3. The phylogenetic tree shows that the strain V903/78 has closest relationship with other tissue adapted vaccine strains.
Figure 4:
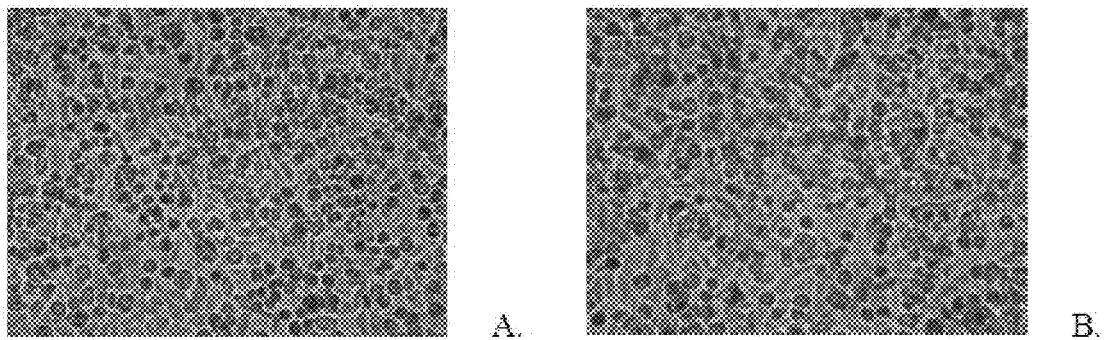
FIG. 4. Replication of an attenuated IBDV strain 903/78 in the human hepatoma cell line. A—HepG2 cell control at 40× magnification. B—IBDV infected HepG2 cells at 40× magnification.
Figure 10:
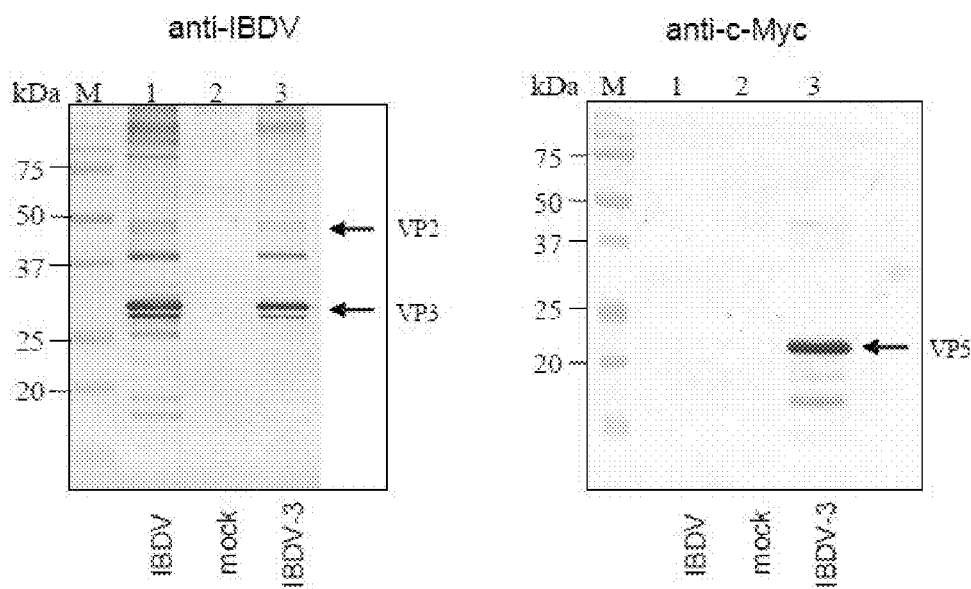
FIG. 10. Immunoblot analysis of IBDV proteins synthesized in virus-infected Vero cells. Vero cells were co-transfected with pIBDVB and pIBDVA or pIBDV-3. After 5 day post-transfection virus was harvested by three cycles of freeze-thaw. The lysed proteins were separated on 12.5% SDS-PAGE, blotted onto nitrocellulose, reacted with polyclonal anti-IBDV rabbit serum (i) and c-Myc monoclonal antibody (Myc1-9E10) (ii) and detected with alkaline-phosphatase and naphtholphosphate fast red color development reagents. Lane 1: IBDV-infected; lane 2: mock infected; lane 3: IBDV-3 infected. The position of VP2, VP3 (i) and VP5 (ii) and marker proteins in kDa (M) are indicated.

The replication kinetics of the attenuated IBDV strain V903/78 was compared in the African green monkey VERO cell line and in the human hepatoma HepG2 cell line. Virus replication was measured by carrying out inoculation in both suspension and in adherent cell cultures, respectively. For testing in suspension cultures, 25 cm² tissue culture flasks were seeded with $10^{6.20}$ $(1.6 \times 10^6)$ VERO cells or with $10^{6.13}$ $(1.4 \times 10^6)$ HepG2 cells, and inoculated at a MOI of approximately 1 at the time of seeding with the IBDV strain V903/78 (Table 1). For testing in confluent adherent cell cultures, the cell counts in 25 cm² tissue culture flasks were $10^{6.46}$ $(2.9 \times 10^6)$ for VERO cultures and $10^{6.39}$ $(2.5 \times 10^6)$ for HepG2 cultures at the time of inoculation (infection) with $10^{6.46}$ $TCID_{50}$ or with $10^{6.39}$ $TCID_{50}$ of IBDV strain V903/78, respectively (Table 1). VERO and HepG2 cells were incubated for 5 days at 37° C. in a 5% CO2 atmosphere; cultures were microscopically monitored every day (at 10, 20 and 40× magnification). Cell free culture supernatants and supernatants containing lysed cells (after a freeze-thawed cycle) were taken at 24 hr intervals up to 120 hr post-inoculation from tissue culture flasks of each type of cell culture. Virus titre determination of samples was done by standard titration method on CEF cell cultures. The results of IBDV V903/78 virus replication in HepG2 and VERO cell lines are summarized in Table 2 below. The achieved virus titre is well above the titre that was previously achieved with similar IBDV strains (Kibenge et al. 1988b). It is very important to note that the IBDV replication was not associated with cytopathic effects in the HepG2 cells (FIG. 4 B).

TABLE 1

Virus titre (log10) and virus/cell ratio in different cell lines at infection time:

| Culture type | Cell line | Cell count at infection (×10⁶ cell/flask) | Titre of virus at inoculum (log10) | Virus/cell ratio |
|---|---|---|---|---|
| Adherent | HepG2 | 2.47 | 6.39 | 0.94 |
|  | VERO | 2.92 | 6.46 | 0.88 |
| Suspension | HepG2 | 1.37 | 6.13 | 0.85 |
|  | VERO | 1.60 | 6.20 | 0.91 |

TABLE 2

Virus titre (log10) in different cell lines at certain sampling time:

|  | 24 h | 48 h | 72 h | 96 h | 120 h |
|---|---|---|---|---|---|
| HepG2 suspension | 3.2 | 5.1 | 6.2 | 7.4 | 7.4 |
| HepG2 adherent | 4.3 | 5.5 | 6.7 | 7.5 | 7.5 |
| VERO suspension | 5.1 | 7.65 | 7.6 | 7.3 | 7.3 |
| VERO adherent | 5.1 | 6.8 | 7.5 | 7.8 | 7.8 |

Example 2

The Construction of a Recombinant IBDV Vector Incorporating a Third Genomic Segment Expressing a Cytokine Methods for generating birnavirus from synthetic RNA transcripts is described in Mundt, E., and Vakharia, V. N.

(1996). Proc Natl Acad Sci USA 93, 11131-11136, U.S. Pat. No. 5,871,744. Full-length molecular cDNA clones of the A (pA903) and B (pB903) segments of the IBDV strain V903/78 are constructed according to the methods in Mundt, E., and Vakharia, V. N. (1996). Proc Natl Acad Sci USA 93, 11131-11136. A third genomic segment, denoted as segment C (pC903-INFb) is constructed to express human INF-beta. The recipient plasmid pB903 is comprised of the B segment that is the 5' and 3' non-coding regions and of the VP1 protein coding region.

First, the INF-beta sequence is amplified by PCR with the INF-beta specific primers:

```
aBb1:
                                        (SEQ. ID. NO: 5)
5'-GGTTCCCATCATGGCTGTTACTGGGATGCTCTTCGACCTC-3' sBb2:
                                        (SEQ. ID. NO: 6)
5'-CCTCTTCTTGATGATTCTGCCACCATGTTAATTCTCTCGGAAACG-
3'.
```

The human INF-beta plasmid from Geneservice Ltd. (Clone: MGC:96956; GenBank number: NM_002176) is used as a template for this reaction.

Then the IBDV 5' and 3' sequences are amplified using the pB903 plasmid as the template and the two sets of outside primers:

```
B5'-903:
                                        (SEQ. ID. NO: 7)
5'-AGAGAATTCTAATACGACTCACTATAGGATACGATGGGTCTGAC-3' aBb2:
                                        (SEQ. ID. NO: 8)
5'-CGTTTCCGAGAGAATTAACATGGTGGCAGAATCATCAAGAAGAGG-
3'
and B3'-903:
                                        (SEQ. ID. NO: 9)
5'-CGATCTGCTGCAGGGGGCCCCCGCAGGCGAAGG-3' sBb1:
                                        (SEQ. ID. NO: 10)
5'-GAGGTCGAAGAGCATCCCAGTAACAGCCATGATGGGAACC-3'
```

Next aliquots from the two previous reactions are mixed and primers B5'-903 and B3'-903 are used to amplify the complete new sequence (FIG. 5). The PCR product is purified and digested with Pst I and EcoRI restriction enzymes and cloned into the Pst I (5' region) and EcoRI (3' region) restriction sites of the pB903 vector resulting in plasmid pC903-INFb. The three plasmids (pA903, pB903 and pC903-INFb) are used as templates for in vitro transcription with T7 RNA polymerase, transfected into VERO cells. Production in the cell supernatant of INF-beta is verified by ELISA and the new virus (903/78INFb) that express INF-beta is selected by standard plaquing.

Example 3

The Construction of a Recombinant IBDV Vector that Incorporates a Cytokine Coding Sequence into an Existing Genomic Segment B The full-length molecular cDNA clone of the B (pB903) segments of the IBDV strain V903/78 constructed according to and methods in Mundt, E., and Vakharia, V. N. (1996) is modified by incorporating a new gene (INF-gamma) front of (proximal) or behind (distal) position of the VP1 coding region. The cDNA constructs are made as in Example 2 with primers shown in FIG. 6. A SmaI restriction site is placed between the two gene-coding sequences (VP1 and INF-gamma) by the use of primers aBg1 and sBg1. The two genes are functionally connected with an internal ribosome entry site (IRES) that is cloned into the SmaI site with blunt end ligation. The IRES is derived from the human eIF4G initiation factor according to Wong et al. (2002) Gene Therapy 9:337-344. The INF-gamma sequence is amplified by PCR with the INF-gamma specific primers shown on FIG. 6. The human INF-gamma plasmid from Geneservice Ltd. (Clone: MGC: 88243; GenBank number: NM_000619) is used as a template for this reaction.

The two plasmids (pA903, and pB903-INFgP) and (pA903, and pB903-INFgD) respectively are used as templates for in vitro transcription with T7 RNA polymerase, transfected into VERO cells. Production in the cell supernatant of INF-gamma is verified by ELISA and the new viruses (903/78INFgP) and (903/78INFgD) that express INF-gamma are selected by standard plaquing.

Example 4

The Construction of a Recombinant IBDV Vector that Incorporates a Cytokine into an Existing Genomic Segment A In this example the non-essential protein VP5 is exchanged for INF-alpha2 and an IRES sequence. Full-length molecular cDNA clones of segment A (pA903) of IBDV strain V903/78 are constructed according to Example 2 and methods in Mundt, E., and Vakharia, V. N. (1996). Proc Natl Acad Sci USA 93, 11131-11136. Plasmid p903A was mutated according to Mundt et al. (1997) J. Virology 71:5647-5651. The start codon of VP5 was changed to Arg from Met and an AflII site was created. Similarly another AflII site was created adjacent to the VP2 start codon resulting in plasmid pA903Afl (FIG. 7). The INF-alpha sequence is amplified by PCR with the INF-alpha specific primers shown on FIG. 7. The human INF-alpha plasmid from Geneservice Ltd. (Clone: MGC: 104046; GenBank number: NM_000605) is used as a template for this reaction. The human eIF4G initiation factor IRES was PCR amplified according to Wong et al. (2002) Gene Therapy 9:337-344., as in Example 3 using primers according to FIG. 7. Aliquots from the two previous reactions are mixed and the two outside primers sAa1 and aAa3 incorporating AflII sites are used to amplify the combined sequence (FIG. 7). The PCR product is purified and digested with AflII restriction enzyme and cloned into the AflII cut pA903Afl plasmid, replacing the 5' region of VP5 coding sequences resulting in plasmid pC903-INFa. The two plasmids (pA903-INFa and pB903) are used as templates for in vitro transcription with T7 RNA polymerase, transfected into VERO cells. Production of INF-alpha in the cell supernatant is verified by ELISA, and the new virus (903/78INFa) expressing INF-alpha is selected by standard plaquing.

Example 5

Generation of Complementing Cell Lines for Recombinant IBDV Growth, Vero-pVP2 and Vero-VP1

IBDV virus is generally cultured in chicken embryo fibroblast cells, but strains of this virus can also be propagated in Vero cells. As Vero cells are easier to maintain in culture it was decided to use these as the basis for the new cell lines. In the first instance a Vero cell line expressing pVP2 (the precursor protein of VP2) was constructed. Another cell line also being constructed that is expresses the VP1 protein in a Vero cell line.

Figure 11:
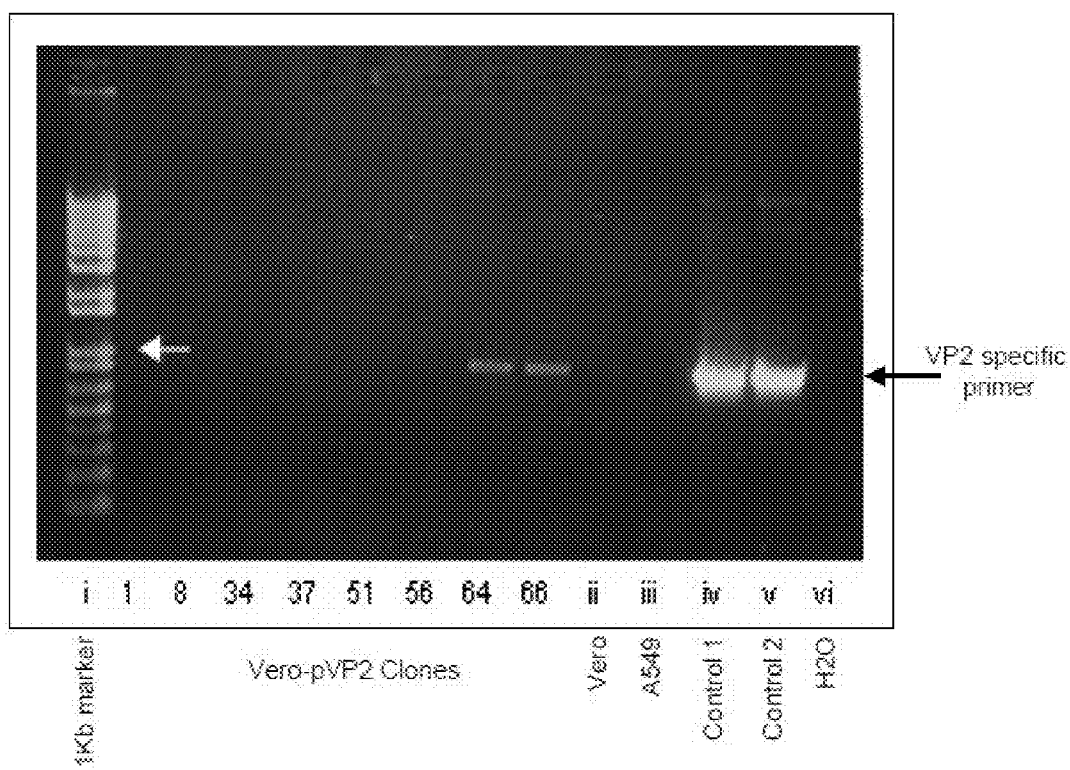
FIG. 11. Generation of a complementing cell line expressing the VP2 gene (Vero-pVP2) allowing for the manufacture of a VP2 deficient IBDV vector by complementarity. Representative examples of PCR screening for positive Vero-pVP2 clones. A VP2 specific primer pair: IBDVP2-F115 5'-aagcacactctcaggtcagagacc-3' and IBDVP2-R1026 5'-atggatcgtcactgctaggctcc-3', was used in PCR on cell genomic DNA to determine if clones were positive (band size at 911 bp). Lanes labeled are: (i) 1 Kb marker, (ii) Vero parental cell line, (iii) A549 negative control cell line, (iv) pRc-CMV-IVS-VP2, (v) pRc-sMT-IVS-VP2, (vi) dH20 control. The clone samples are indicated by their official number below the appropriate lanes.

Although pVP2 is not expected to be toxic to Vero cells two different constructs have been designed, one with a constitutive CMV promoter and another with the zinc inducible sheep metallotheinen (sMT) promoter. Both constructs produced candidate cell lines after puromycin selection indicating that our original assumption was correct. The pVP2 gene from strain V903/78 was synthesized and inserted into their cloning vector pJ241, with NotI and XbaI restriction sites flanking the 5' and 3' ends respectively. Than pVP2 sequence was excised with NotI/XbaI and subcloned into the NotI/XbaI sites in two plasmids: pRc-CMV-IVS-Puro and pRc-sMT-IVS-Puro. These plasmids contain the CMV and the zinc inducible sheep metallotheinen (sMT) promoters respectively as well a synthetic intron, directly following the promoter to enhance expression of the gene. Linearized plasmids were transfected with Qiagen Superfect reagent into Vero cells, selected with media containing 3.75 ug/ml puromycin. Following 15 days in selection media 42 colonies were ring cloned and genome DNA was then extracted using the DNeasy kit (Qiagen) and tested in PCR with VP2 specific primers (FIG. 11). Any clone that tested positive with the analytical PCR was then further propagated and vials of cells frozen down. With respect to analyzing expression of pVP2 in sMT clones, media is switched to that containing no zinc or zinc sulphatesulfate (final concentration in media at 100 uM) to induce the sMT promoter. At 48 h following culture in zinc media cells are harvested and analyzed for pVP2 expression through RT-PCR and western blot analysis.

To be able to replace the VP1 gene in the IBDV genome with another gene (e.g INF-alpha) a cell line expressing the VP1 gene is needed. The VP1 defective virus construct need to be transfected into the VP1 complementing cell line (Vero-VP1) as this virus is replication defective in any other cell line as it has no functional RNA-polymerase expression of its own. Production in the cell supernatant of IFN-alpha is verified by ELISA. Generation of a complementing cell line for VP1 is proceeding essentially the same way as the Vero-pVP2 cell line construction described above. Over expression of VP1 might be toxic to Vero cells, therefore again both the constitutive CMV promoter and the sMT promoter is used.

All of the references cited herein, including patents, patent applications, and publications, are hereby incorporated in their entireties by reference.

While this invention has been described with an emphasis upon some preferred embodiments, variations of the preferred embodiments can be used, and it is intended that the invention can be practiced otherwise than specifically described herein. Accordingly, this invention includes all modifications encompassed within the spirit and scope of the invention as defined by the following claims.

REFERENCES

1. Ben Abdeljelil N, Khabouchi N and Mardassi H (2008). Efficient rescue of infectious bursal disease virus using a simplified RNA polymerase II-based reverse genetics strategy. Arch Virol 153: 1131-1137.
2. Bayliss, C. D., Spies, U., Shaw, K., Peters, R. W., Papageorgiou, A., Muller, H., and Boursnell, M. E. (1990). A comparison of the sequences of segment A of four infectious bursal disease virus strains and identification of a variable region in VP2. J Gen Virol, 71, 1303-1312.
3. Bakacs, T., and Mehrishi, J. N. (2002). Intentional superinfection of decompensated chronic viral hepatitis by avian infectious bursal disease virus shows promise. Paper presented at: Cancer Detection and Prevention.
4. Bakacs, T., and Mehrishi, J. N. (2004). Examination of the value of treatment of decompensated viral hepatitis patients by intentionally coinfecting them with an apathogenic IBDV and using the lessons learnt to seriously consider treating patients infected with HIV using the apathogenic hepatitis G virus. Vaccine 23, 3-13.
5. Boot, H. J., Dokic, K., and Peeters, B. P. (2001). Comparison of RNA and cDNA transfection methods for rescue of infectious bursal disease virus. J Virol Methods 97, 67-76.
6. Boot, H. J., ter Huurne, A. A., Hoekman, A. J., Peeters, B. P., and Gielkens, A. L. (2000). Rescue of very virulent and mosaic infectious bursal disease virus from cloned cDNA: VP2 is not the sole determinant of the very virulent phenotype. J Virol 74, 6701-6711.
7. Csatary, L. K., Kasza, L., and Massey, R. J. (1984). Interference between human hepatitis A virus and an attenuated apathogenic avian virus. Acta Microbiol Hung 31, 153-158.
8. Csatary, L. K., Schnabel, R., and Bakacs, T. (1999). Successful treatment of decompensated chronic viral hepatitis by bursal disease virus vaccine. Anticancer Res 19, 629-633.
9. Csatary, L. K., Telegdy, L., Gergely, P., Bodey, B., and Bakacs, T. (1998). Preliminary report of a controlled trial of MTH-68/B virus vaccine treatment in acute B and C hepatitis: a phase II study. Anticancer Res 18, 1279-1282.
10. Galle, P. R., Schlicht, H. J., Fischer, M. and Schaller, H. (1988). Production of infectious duck hepatitis B virus in a human hepatoma cell line. J Virol 62, 1736-1740.
11. Jackwood, D. J., and Sommer, S. E. (2002). Identification of infectious bursal disease virus quasispecies in commercial vaccines and field isolates of this double-stranded RNA virus. Virology 304, 105-113.
12. Kibenge, F. S., Dhillon, A. S., and Russell, R. G. (1988a). Biochemistry and immunology of infectious bursal disease virus. J Gen Virol 69 (Pt 8), 1757-1775.
13. Kibenge F S, Dhillon A S and Russell R G (1988b). Growth of serotypes I and II and variant strains of infectious bursal disease virus in Vero cells. Avian Dis 32: 298-303.
14. Kwon H M and Kim S J (2004). Sequence analysis of the variable VP2 gene of infectious bursal disease viruses passaged in Vero cells. Virus Genes 28: 285-291.
15. Lim B L, Cao Y, Yu T and Mo C W (1999). Adaptation of very virulent infectious bursal disease virus to chicken embryonic fibroblasts by site-directed mutagenesis of residues 279 and 284 of viral coat protein VP2. J Virol 73: 2854-2862.
16. Mundt, E. Kollner, B. and Kretzschmar, D. (1997). VP5 of infectious bursal disease virus is not essential for viral replication in cell culture. J Virol 71, 5647-5651.
17. Mundt, E., and Vakharia, V. N. (1996). Synthetic transcripts of double-stranded Birnavirus genome are infectious. Proc Natl Acad Sci USA 93, 11131-11136.
18. Pedersden, K. A., Sadasiv, E. C., Chang, P. W., and Yates, V. J. (1990). Detection of antibody to avian viruses in human populations. Epidemiol Infect 104, 519-525.
19. Walters, K-A., Joyce, M. A., Addison, R. W., Fischer, K. P. and Tyrrell, D. L. J. (2004). Superinfection Exclusion in Duck Hepatitis B Virus Infection Is Mediated by the Large Surface Antigen. J Virol 78, 7925-7937.
20. Wong, E-T., Ngoi, E-T. and Lee, C. G. L. (2002) Improved co-expression of multiple genes in vectors containing internal ribosome entry sites (IRESes) from human genes. Gene Therapy 9, 337-344
21. Ye J, Chen Q, Zhou J and Li L (2007). Cloned Vero cell lines transfected with full-length A-segment or ORF1 cDNA sequence of IBDV. Cell Biol Int 31: 165-172.
22. Zierenberg, K., Raue, R., Nieper, H., Islam, M. R., Eterradossi, N., Toquin, D., and Muller, H. (2004). Generation of serotype 1/serotype 2 reassortant viruses of the infectious bursal disease virus and their investigation in vitro and in vivo. Virus Res 105, 23-34.

The invention claimed is:

1. A composition selected from the group consisting of (i) an Infectious Bursal Disease Virus (IBDV) strain which can be grown in the HepG2 human liver cell line without causing detrimental effects to the cells, said strain comprising the RNA nucleotide sequences SEQ ID NO:1 and SEQ ID NO:2;

(ii) a recombinant IBDV vector comprising the nucleotide sequence of the IBDV strain; and (iii) a pharmaceutical preparation comprising the IBDV strain or the IBDV vector, and a suitable carrier or excipient.

2. The composition of claim 1, which is the recombinant IBDV vector comprising the nucleotide sequence of the IBDV strain and further comprising an exogenous nucleic acid sequence.

3. The composition of claim 2, wherein the vector comprises an expression control sequence operably linked to the exogenous nucleic acid sequence.

4. The composition of claim 2, wherein the exogenous nucleic acid sequence encodes a cytokine and wherein the expression control sequence is operably linked to the exogenous nucleic acid sequence.

5. The composition of claim 4, wherein the encoded cytokine belongs to the family of interferons.

6. The composition of claim 1, which is the pharmaceutical preparation comprising,
    the IBDV strain or the IBDV vector and
    a suitable carrier or excipient.

7. The composition of claim 6 comprising $10^{5.0}$-$10^{8.0}$ $TCID_{50}$ active viruses of the strain per unit dose.

* * * * *